(12) United States Patent
Taylor et al.

(10) Patent No.: US 6,407,201 B1
(45) Date of Patent: Jun. 18, 2002

(54) PLASTICIZERS FOR BOWLING BALL COVERSTOCKS

(75) Inventors: Ronald P. Taylor, Moon Township; Jeffrey A. Dodge, Weford, both of PA (US); Hartmut Nefzger, Pulheim (DE)

(73) Assignee: Bayer Corporation, Pittsburgh, PA (US)

(*) Notice: Subject to any disclaimer, the term of this patent is extended or adjusted under 35 U.S.C. 154(b) by 0 days.

(21) Appl. No.: 09/644,110

(22) Filed: Aug. 21, 2000

(51) Int. Cl.[7] .................. C08G 63/181; C08G 63/16; C07C 69/67; C07C 69/80
(52) U.S. Cl. .......... 528/272; 528/308; 560/76; 560/79; 524/315
(58) Field of Search .............. 560/76, 795; 524/306, 524/315; 528/272, 308

(56) References Cited

U.S. PATENT DOCUMENTS

| | | |
|---|---|---|
| 4,263,408 A | 4/1981 | Meyborg et al. .............. 521/51 |
| 4,316,987 A * | 2/1982 | Ceprini et al. |

* cited by examiner

Primary Examiner—Tae H. Yoon

(74) Attorney, Agent, or Firm—Joseph C. Gil; Noland J. Cheung; Lyndanne M. Whalen

(57) ABSTRACT

The present invention provides a plasticizer compound having the general formula:

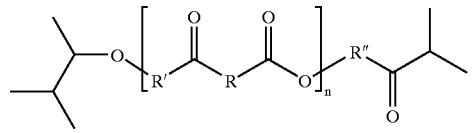

in which n=1 to 3, R represents a $C_2$–$C_8$ straight or branched aliphatic hydrocarbon chain or $C_6$–$C_{10}$ aromatic or cycloaliphatic group, and R' and R'' are each independently a branched oxyalkylene chain represented by the chemical formula $C_8H_{16}O$ and by the chemical structures:

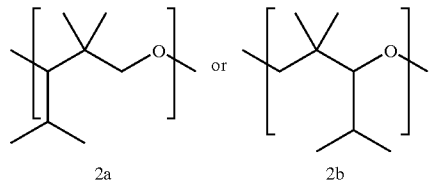

2a      2b

The present invention is also directed to a coverstock formulation comprising the above-plasticizer compound.

5 Claims, No Drawings

PLASTICIZERS FOR BOWLING BALL COVERSTOCKS

FIELD OF THE INVENTION

The invention relates to a plasticizer, which can be used in coverstocks for bowling balls.

BACKGROUND OF THE INVENTION

Polyurethane raw materials have been used for bowling ball coverstocks for many years. Polyurethanes are used industry-wide for professional bowling balls (and high-end amateur products) because they provide the necessary on-lane performance required at this high level of play.

In the game of bowling, a skillful bowler generally rolls the ball down the bowling lane such that the bowling ball enters the pin placement at an angle with respect to longitudinal axis of the bowling ball. It is generally known that the larger the angle the bowling ball travels before it hits the pins, the larger the area of impact with the pins, thereby resulting in more pins being knocked down or if all ten pins are knocked down, a "strike" is thrown.

Therefore, of particular importance is the ability of the ball to "hook" near the end of the bowling lane when thrown with spin. The bowling community calls this hooking performance "reactivity" and a ball that hooks well is known as a "reactive ball."

One of the most important formulation ingredients contributing to ball reactivity is the plasticizer. Plasticizers such as 2,2,4-trimethyl-1,3-pentanediol diisobutyrate (Kodaflex "TXIB"), from Eastman Chemical Company, are used in polyurethane formulations for application as coverstocks.

An object of the present invention is to provide a bowling ball which is less sensitive to the effects of the oil on a bowling lane. The plasticizers of the present invention achieve this result.

SUMMARY OF THE INVENTION

There is still, therefore, a need to create a bowling ball with better ball performance than the bowling balls having the conventional coverstocks.

Accordingly, the present invention provides plasticizer compounds represented by the formula:

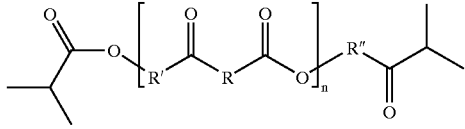

in which n=1 to 3, R represents a $C_2$–$C_8$ straight or branched aliphatic hydrocarbon chain or $C_6$–$C_{10}$ aromatic or cycloaliphatic group, and R' and R" are each independently a branched oxyalkylene chain represented by the chemical formula $C_8H_{16}O$ and by the chemical structures:

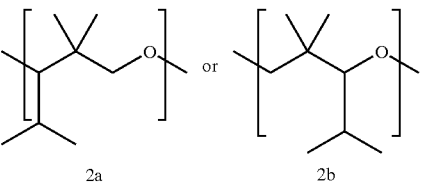

The present invention is also directed to a coverstock formulation comprising the plasticizer compound (1).

DETAILED DESCRIPTION OF THE INVENTION

The present invention relates to a plasticizer compound having the general formula:

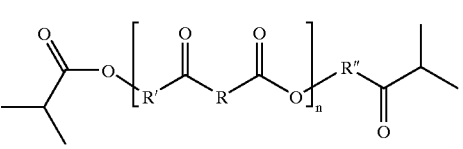

in which n=1 to 3, R represents a $C_2$–$C_8$ straight or branched aliphatic hydrocarbon chain or $C_6$–$C_{10}$ aromatic or cycloaliphatic group, and R' and R" are each, independently, groups represented by the chemical formula $C_8H_{16}O$ and by the chemical structures:

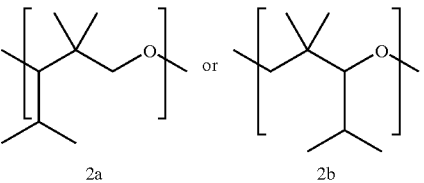

R is understood to mean $C_2$–$C_8$ alkylene chains, $C_6$–$C_{10}$ cycloalkylene chains or $C_6$–$C_{10}$ arylene chains. In the case that R represents a $C_2$–$C_8$ alkylene chain, $C_2$–$C_8$ alkylenes are to be understood to mean all linear or branched alkylene residues with 2 to 8 carbon atoms, such as, ethylene, n-propylene, i-propylene, n-butylene, i-butylene, n-pentylene, i-pentylene, neopentylene and hexylene, which, in turn, may again be substituted. By way of substituents in this connection, halogen, or $C_2$–$C_8$ alkyl or alkoxy, as well as $C_6$–$C_{10}$ cycloalkyl or $C_6$–$C_{10}$ aryl, come into consideration, such as chloroethylene, cyclohexylethylene or phenylethylene.

In the case that R represents a $C_6$–$C_{10}$ cycloalkylene chain, $C_6$–$C_{10}$ cycloalkylene is to be understood to mean all mononuclear or polynuclear cycloalkylene residues with 6 to 10 carbon atoms, such as cyclohexylene, cycloheptylene, which, in turn, may again be substituted. By way of substituents in this connection, halogen or also $C_2$–$C_8$ alkyl or alkoxyl, as well as $C_6$–$C_{10}$ cycloalkyl or $C_6$–$C_{10}$ aryl, come into consideration. $C_6$–$C_{10}$ cycloalkylene can also include structures with fatty hydrocarbon chains pendant from a cycloaliphatic ring, such as products derived from the materials collectively referred to as "dimer acids". In this. case, even though the total structural fragment separating the ester carbonyl groups is greater that $C_6$–$C_{10}$ (typically around $C_{36}$), the chain directly connecting the carbonyl groups is still in the range of $C_6$–$C_{10}$.

$C_6$–$C_{10}$ arylene is to be understood to mean all mononuclear or polynuclear aryl residues with 6 to 10 carbon atoms, such as phenylene or naphthylene, which, in turn, may again be substituted. By way of substituents in this connection, halogen, or also $C_2$–$C_8$ alkyl or alkoxyl, as well as $C_6$–$C_{10}$ cycloalkyl or $C_6$–$C_{10}$ aryl, come into consideration.

Preferred embodiments of the present invention include examples in which R represents an octamethylene chain, a tetramethylene chain or a 1,2-phenylene group.

Examples of plasticizer compounds of the present invention include di-Texanol sebacate, and di-Texanol adipate and di-Texanol phthalate having. the following simplified structures, respectively:

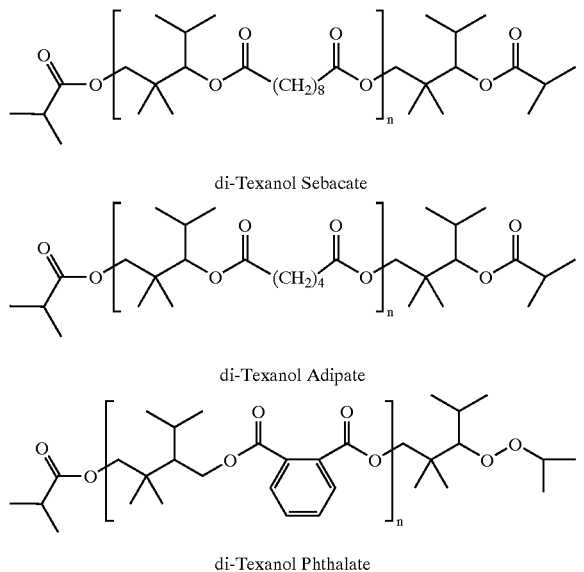

di-Texanol Sebacate di-Texanol Adipate di-Texanol Phthalate

During the preparation of the plasticizer compounds of the present invention from one mole of dicarboxylic acid and two moles of the mono-hydroxy compound "Texanol," which is a registered trademark of Eastman Chemical Company, (2,2,4-trimethyl-1,3-pentanediol monoisobutyrate), the major product is the 2:1 adduct represented by the structure with n=1. However, small amounts of the product corresponding to the structure with n=2 or n=3 may be present from reaction of the carboxylic acid reactant with traces of 2,2,4-trimethyl-1,3-pentanediol in the 2,2,4-trimethyl-1,3-pentanediol monoisobutyrate, or from transesterification of one of the isobutyrate groups. Further, since the monoisobutyrate material used for preparation of the plasticizer products contains a mixture of isomers, the plasticizer compounds of the invention also includes an isomeric mixture. Small amounts of 2,2,4-trimethyl-1,3-pentanediol diisobutyrate may also be present as a trace contaminant.

The plasticizer compound of the present invention can also be used as a plasticizer for PVC, as an additive for coatings or as part of wood preserving formulations. Such plasticizers may also be used as plasticizers in normal (soft) polyurethane elastomers. Most preferably, the plasticizer compound is used in a bowling ball coverstock to make a bowling ball.

The bowling ball coverstock of the present invention comprises at least one isocyanate, at least one active hydrogen-containing compound and various additives including the above-mentioned plasticizer compound of the present invention.

As isocyanates, those that are used, are aliphatic, cycloaliphatic, araliphatic, aromatic and heterocyclic polyisocyanates, such as those described, for example, by W. Siefken in Justus Liebigs Annalen der Chemie, 562, pp. 75–136, for example, those of the formula $Q(NCO)_n$ in which n denotes 2–4, preferably 2–3, and
Q denotes an aliphatic hydrocarbon radical of 2–18, preferably 6–10 carbon atoms, a cycloaliphatic hydrocarbon radical of 4–15, preferably 5–10 carbon atoms, an aromatic hydrocarbon radical of 6–15, preferably 6–13 carbon atoms or an araliphatic hydrocarbon radical of 8–15, preferably 8–13 carbon atoms, for example, such polyisocyanates as described in DE-OS 2,832,253, pp 10–11.

Particularly preferred are usually those polyisocyanates which are technically readily accessible, for example, the 2,4- and 2,6-toluylene diisocyanate as well as any mixture of these isomers ("TDI"); polyphenyl-polymethylenepolyisocyanates, such as those obtained by an aniline-formaldehyde condensation and subsequent treatment with phosgene ("crude MDI"), and polyisocyanates comprising carbodiimide groups, urethane groups, allophanate groups, isocyanurate groups, urea groups or biuret groups ("modified polyisocyanates"), especially those modified polyisocyanates which are derived from 2,4- and/or 2,6-toluylene diisocyanate and from 4,4'- and/or 2,4'- diphenylmethane diisocyanate. In a particularly preferred embodiment, a 131 equivalent weight polymeric isocyanate mixture having about 50% monomeric 4,4'-MDI, about 3% monomeric 2,4'- and 2,2'-MDI isomers and about 57% higher molecular weight homologues of the MDI series is desired.

The starting components may further be compounds of a molecular weight usually of 400 to 10,000, containing at least two hydrogen atoms reactive toward isocyanates. These comprise, besides .compounds containing amino, thio, or carboxyl groups, preferably compounds containing hydroxyl groups, in particular compounds containing 2 to 8 hydroxyl groups, especially those of a molecular weight of 400–8000, preferably 600 to 4000, for example, polyethers and polyesters as well as polycarbonates and polyester amides containing at least 2, usually 2 to 8, preferably 2 to 6 hydroxyl groups; these compounds are known per se for the preparation of homogenous and cellular polyurethanes and are disclosed, for example in DE-OS 2,832,253, pp. 11–18.

When appropriate, compounds comprising at least two hydrogen atoms reactive toward isocyanates and of a molecular weight of 32 to 399 may be used as further starting components. Also, in this case, compounds containing hydroxyl groups and/or amino groups and/or thiol groups and/or carboxyl groups, preferably compounds containing hydroxyl groups and/or amino groups, are understood to be those which are used as chain extenders or crosslinking agents. These compounds usually have 2 to 8, preferably 2 to 4 hydrogen atoms reactive toward isocyanates. Appropriate examples are disclosed in DE-OS 2,832, 253, pp. 19–20.

Other compounds known to be useful in polyurethane formulations can also be used, including catalysts, surfactants, viscosity modifiers, stabilizers, release agents, drying agents, fillers and reinforcements.

EXAMPLES

Description of the Materials

Polyol A: A tetrafunctional polyether polyol prepared by addition of propylene oxide to ethylene diamine, characterized by a hydroxyl number of approximately 770 and a viscosity at 25° C. of around 36,000 mPa·sec.

Polyol B: A trifunctional polyether polyol prepared by addition of propylene oxide to glycerine, characterized by a hydroxyl number of approximately 250 and a viscosity at 25° C. of around 250 mPa·sec.

Polymeric Isocyanate: A polymeric diphenylmethanediisocyanate with a % NCO of approximately 31.9 and a viscosity at 25° C. of approximately 200 mPa·sec.

Molecular Sieve Drying Agent: A powdered form of synthetic zeolites used as a moisture scavenger.

The following examples discuss the preparation of the di-Texanol carboxylate plasticizers of the present invention.

Example 1

Synthesis of di-Texanol Sebacate 11,183 g of toluene, 16,413 g of 2,2,4-trimethyl-1,3-pentanediol monoisobutyrate (Texanol), 4,605 g (22.8 moles) of sebacic acid, and 8.6 g (500 ppm) of p-toluenesulfonic acid monohydrate were added to a 15 gallon steel reaction vessel equipped with a mechanical stirrer, a reflux condenser and a Dean-Starck trap. The Dean-Starck trap was filled with toluene, the vessel was flushed with dry nitrogen, and stirring and heating were started. The temperature was gradually raised until the solvent started to reflux. After 17 hours, 333 g of water had been collected in the trap. An additional 10 g of p-toluene sulfonic acid monohydrate was added and refluxing was continued for an additional 48 hours, whereby a total of 860 g of water had been collected in the trap (theoretical, 820 g). The trap was then replaced with a distillation column and the toluene was distilled off under vacuum to leave an oily liquid product. Analysis of the product showed a hydroxyl number of 11.6 mg KOH/g, and an acid number of 0.010 mg KOH/g.

Example 2

Synthesis of di-Texanol Adipate

The adipate was synthesized by a method analogous to that of the sebacate of Example 1, except that adipic acid was substituted on an equimolar basis for the sebacic acid. From 1100 g (2.6 moles) of Texanol and 189.8 g (1.3 moles) of adipic acid in 700 g of toluene, and after removal of the solvent, 1103 g of oily liquid product with a hydroxyl number of −4.6 mg KOH/g (uncorrected) and an acid number of 0.209 mg KOH/g was obtained. Analysis by gel permeation chromatography (GPC) and nuclear magnetic resonance spectroscopy (NMR) confirmed that the product mixture falls within the description of structure 1, with ca. 73% n=1, ca. 18% n=2, and ca. 4% n=3.

Example 3

Synthesis of di-Texanol Phthalate

The phthalate of Texanol was prepared from the acid chloride (i.e., phthaloyl dichloride) using the well-established Schotten-Baumann technique, instead of from the free acid. 420 g of Texanol (2 mol) and 260 g (3 moles) of pyridine were added to a 2 liter glass flask equipped with a mechanical stirrer, dropping funnel, thermometer and drying tube. The mixture was cooled to 10° C. in an ice bath, then 200 g (1 mole) of phthaloyl dichloride was added dropwise with stirring. The rate of addition was controlled to keep the temperature below 15° C. After stirring for 60 minutes, the ice bath was removed and the temperature was allowed to increase to ambient. Stirring was continued for an additional 2. hours, then discontinued and the reaction mixture allowed to stand overnight. One (1) liter of ice water was added to the flask, then concentrated HCl solution was added until the pH reached a value of 3. The crude reaction mixture was transferred to a separatory funnel. One (1) liter of methylene chloride was added, and the layers separated. The (lower) methylene chloride layer was washed with 500 ml of half-saturated sodium bicarbonate solution (prepared by diluting 250 ml of a saturated solution with 250 ml of water), then dried overnight over sodium sulfate. The solution was then filtered to remove the drying agent, and the solvent evaporated to yield 420 g of an oily liquid product with a hydroxyl number of 18 mg KOH/g and an acid number of 1.78 mg KOH/g.

The following examples relate to the evaluation of di-Texanol carboxylates in plaques of a bowling ball formulation:

Example 4

Evaluation of the di-Texanol Sebacate

In a 1-quart wide-mouthed glass jar, 19.89 g of Polyol B, 53.35 g of di-Texanol sebacate, and 3.00 g of Molecular Sieves Drying Agent were combined to form a mixture. 23.76 g of Polyol A, which had been heated to 70° C. to decrease its viscosity to a workable level was added to the mixture. The mixture was then stirred to a homogeneous blend and allowed to sit overnight at ambient temperature to allow the drying agent to absorb any residual moisture. On the following day, the mixture was re-blended and de-gassed under vacuum. Its viscosity was measured to be 100 mPa·sec at 24° C. A quantity of 80 g of the blend was removed and blended for 45 seconds with 45.14 g of Polymeric Isocyanate. A slight exotherm was observed and a gel time of 1 minute, 52 seconds was measured. The mixture was poured into a 6"×6"×⅛" aluminum plaque mold that had been pre-heated to 70° C. After 15 minutes, the plaque was removed from the mold and examined. The plaque was placed in an oven at 70° C. and allowed to post-cure for 16 hours. After removal from the oven, the plaque was allowed to stand at ambient conditions, and Shore D hardness was measured periodically. After 6 hours, the hardness was measured as 77 initially, 75 after 1 second, and 73–74 after seconds. The hardness did not change in subsequent measurements over a 13-day period.

Example 5

Evaluation of the di-Texanol Adipate

In a 1-quart wide-mouthed glass jar, 20.5 g of Polyol B and 55.0 g of di-Texanol adipate were combined to form a mixture. 24.5 g of Polyol A, which had been heated to 70° C. to decrease its viscosity to a workable level, was added to the mixture. The viscosity of the blend was measured to be 80 mPa·sec at 19° C. A quantity of 80 g of the blend was removed and blended for 45 seconds with 46.55 g of Polymeric Isocyanate. A gel time of 3 minutes, 20 seconds was measured for the reaction mixture. The mixture was poured into a 6"×6"×⅛" aluminum plaque mold that had been pre-heated to 70° C. After 15 minutes, the plaque was removed from the mold and examined. The plaque was placed in an oven at 70° C. and allowed to post-cure for 16 hours. After removal from the oven, the plaque was allowed to stand at ambient conditions, and Shore D hardness was measured periodically. After 1 day, the hardness was measured as 75 initially, 73 after 1 second, and 71 after 5 seconds. The hardness remained within +/−2 points of the original values in subsequent measurements over a 18-day period.

Example 6

The Molding of Bowling Balls Containing di-Texanol Sebacate

Experimental formulations were pre-tested by casting of hand-mixed blends in the laboratory, for subsequent evaluation in bowling balls. Cylindrical "buttons" of 1" diameter and ½" thickness were hand cast and hardnesses measured on the Shore D scale with a durometer. The formulation was adjusted by raising the hydroxyl number (increasing the proportion of Polyol A) of the blend until the desired hardness (74–75 Shore D) was reached. The resulting formulation was:

| | |
|---|---|
| Polyol A | 29 parts |
| Polyol B | 13 parts |
| di-Texanol sebacate | 57 parts |
| Molecular Sieves Drying Agent | 1 part |
| Polymeric Isocyanate | 65.1 parts/100 parts of polyol blend at 1.05 index |

Test specimens for evaluation of mechanical properties were prepared by dispensing a hand-mixed reaction mixture into an 8"×16"×⅛" rectangular aluminum plaque tool containing cavities in the shape of the required types of test specimens. After aging the panels under ambient conditions for approximately 1 week, the following properties were measured:

| | |
|---|---|
| Tensile Strength, lb./in$^2$ | 2914 |
| Elongation, % | 4 |
| Tear Strength, Die C, lb./in. | 65 |
| Flexural Modulus, lb./in$^2$ | 174,764 |
| Izod Impact Strength, ft.-lb./in. | 0.53 |
| Taber Abrasion mg wt. loss/1000 cycles | 888 |

Bowling balls containing the experimental formulations were prepared by dispensing the reaction mixture from an Edge-Sweets Flexamatic model 15BT low-pressure machine at an output of 5.70 lb./minute. From the machine, the reaction mixture had a gel time of approximately 1 minute, 5 seconds at 73° F. For molding of balls, the reaction mixture was injected into a spherical aluminum mold containing a pre-formed spherical calcium carbonate composite core. The mold was pre-heated in an oven, and was at approximately 170° F. at the time of injection. Core weights were approximately 11.4 lb. Balls were demolded after being allowed to cure for 10 minutes at 185° F. or for 15 minutes at 160° F. Balls were made in quadruplicate for on-lane evaluation.

Example 7

On-lane Evaluation of Bowling Balls Made with di-Texanol Sebacate as Plasticizer Experimental balls were machined to size and polished by a standard production procedure to a nominal weight of 16 lb. Drilling of finger holes was customized to the right-handed professional staff bowler assigned to do the evaluation. After the balls were rolled several times to condition them, the lanes were prepared by applying a fresh coat of standard lane oil. The professional staff bowler evaluated the experimental balls by rolling them alternately with balls made from a commercial comparison formulation.

The professional staff bowler assessed the balls by determining the dependence of hooking performance on the position at which he lined up on the approach, and on the position of the target for releasing the ball on the lane.

From the bowler's normal starting position (towards the outside of the approach), it was found that the balls of the formulation of the present invention hooked more strongly than balls of the comparison formulation at the desired mid-range to far end of the lane. Because of this, the bowler was able to adjust position to 3–5 boards to the left of the bowler's normal stance, throw the ball at a target 1–2 boards to the left of the normal target, and still get strong entrance of the ball into the "pocket" of the pins. This strong hooking action into the pocket is desirable for attaining good scores.

In a separate set of evaluations, the bowler was positioned towards the center of the approach and deliberately threw the ball through the center of the lane, where the concentration of lane oil was heavier. From this position, the balls of the experimental formulation of the present invention were found to still perform well, by hooking strongly into the pocket. From this position, balls of the comparison formulation were found to be not controllable. The comparison balls were commercially available Brunswick Green "Control Zone" balls. The balls were observed to slide too much through the section of the lane with the heavy oil concentration, and never did hook strongly into the pocket. Even with adjustments of the starting position on the approach, the bowler was not able to make the comparison ball match the performance of the balls of the experimental formulation of the present invention through the section of the lane with the heavy oil concentration.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A plasticizer compound represented by the formula:

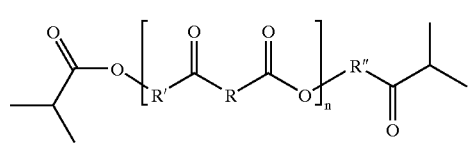

in which n=1 to 3, R represents a $C_2$–$C_8$ straight or branched aliphatic hydrocarbon chain or $C_6$–$C_{10}$ aromatic or cycloaliphatic group, and R' and R" are each independently a branched oxyalkylene chain represented by the chemical formula $C_8H_{16}O$.

2. A plasticizer compound according to claim 1, wherein in said compound, R=$(CH_2)_4$.

3. A plasticizer compound according to claim 1, wherein in said compound, R=$(CH_2)_8$.

4. A plasticizer compound according to claim 1, wherein in said compound,

R = 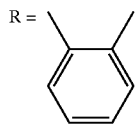

5. A plasticizer composition wherein said composition is a mixture of oligomers represented by a plasticizer compound represented by the formula:

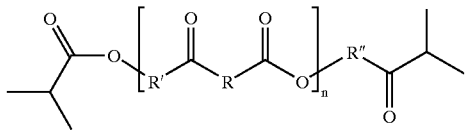

in which n=1 to 3, R represents a $C_2$–$C_8$ straight or branched aliphatic hydrocarbon chain or $C_6$–$C_{10}$ aromatic or cycloaliphatic group, and R' and R" are each independently a branched oxyalkylene chain represented by the chemical formula $C_8H_{16}O$, with greater than 50% of the composition having n=1.

* * * * *